US00PP29956P3

(12) United States Plant Patent
Bull

(10) Patent No.: US PP29,956 P3
(45) Date of Patent: Dec. 4, 2018

(54) **VARIETY OF *RUDBECKIA* PLANT NAMED 'BULLRUDI 02'**

(50) Latin Name: ***Rudbeckia hirta* L.**
Varietal Denomination: BullRudi 02

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 24 days.

(21) Appl. No.: 15/530,061

(22) Filed: Nov. 29, 2016

(65) Prior Publication Data

US 2017/0164545 P1 Jun. 8, 2017

Related U.S. Application Data

(60) Provisional application No. 62/386,453, filed on Dec. 2, 2015.

(51) Int. Cl.
*A01H 5/02* (2018.01)

(52) U.S. Cl.
USPC ..... Plt./474
CPC ..... *A01H 5/02* (2013.01)

(58) Field of Classification Search
USPC ..... Plt./474
CPC ..... A01H 5/02; A01H 5/00
See application file for complete search history.

*Primary Examiner* — Kent L Bell
(74) *Attorney, Agent, or Firm* — The Webb Law Firm

(57) ABSTRACT

A new and distinct variety of *rudbeckia* plant having a compact growth habit with numerous long-lasting and large blooms.

2 Drawing Sheets

Botanical classification: *Rudbeckia hirta* L.
Varietal denomination: 'BullRudi 02'.

BACKGROUND OF THE INVENTION

The present invention comprises a new and distinct cultivar of *rudbeckia* plant known by the varietal name 'BullRudi 02'. The new variety was discovered in October of 2013 in Gönnebeck, Germany as the result of a planned breeding program with the purposes of providing *rudbeckia* plants with improved growth, foliage, and blooms, including developing new color combinations of *rudbeckia* blooms. The new variety is the result of a naturally occurring branch mutation of *Rudbeckia hirta* L. variety named 'BullRudi 01' (allowed U.S. Plant patent application Ser. No. 15/530,059). The new variety is similar to 'BullRudi 01' in botanical classification, but exhibits different colors of its ray and disc florets than those of 'BullRudi 01'. When 'BullRudi 02' is compared to *Rudbeckia hirta* L. variety named 'Prärie Sun' (unpatented), 'BullRudi 02' is similar to 'Prärie Sun' in botanical classification, but 'BullRudi 02' exhibits improved plant quality, plant strength, growth, foliage, and larger blooms that differ in color from those of 'Prärie Sun'. Further, the following characteristics distinguish 'BullRudi 02' when generally compared to other *rudbeckia* varieties known to the breeder:

Good self-branching;
An upright and compact growth habit;
Healthy, clean, and medium-sized foliage;
Long-lasting and large blooms; and
Differing bloom color.

'BullRudi 02' has been trial and field tested and has been found to retain its distinctive characteristics and remain true to type through successive propagations.

DESCRIPTION OF THE DRAWINGS

The accompanying photographic drawings illustrate the new variety at 18 weeks of age, with the color being as nearly true as is possible with color illustrations of this type.

DESCRIPTION OF THE PLANT

Figure 1:
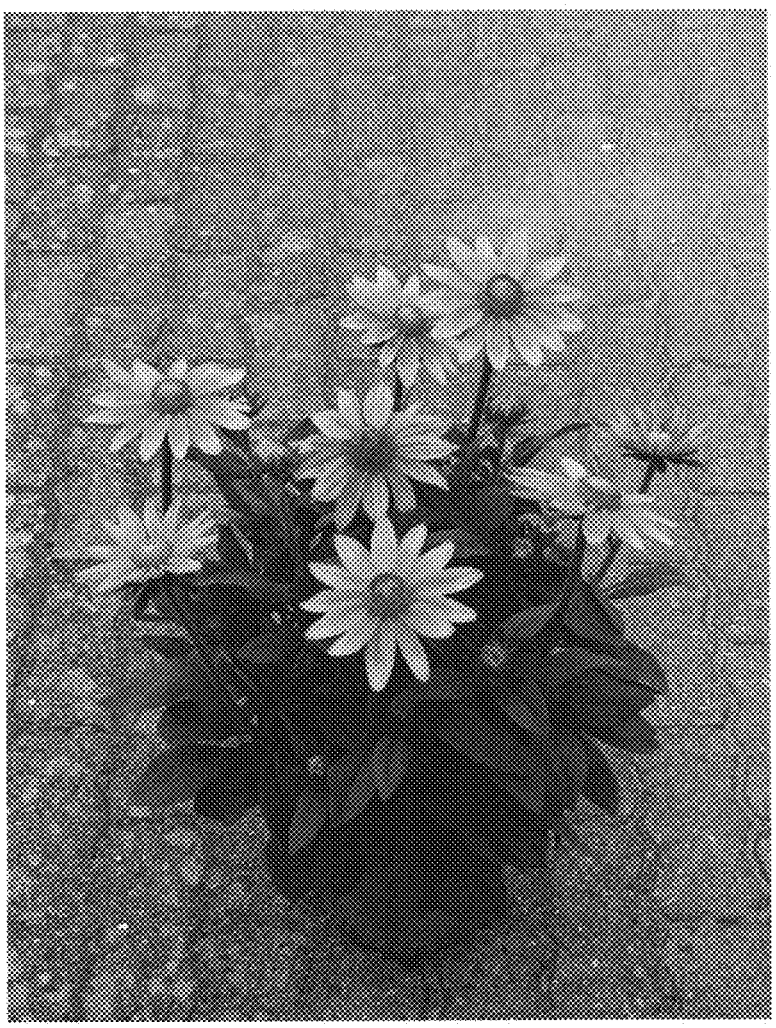
FIG. 1 shows an entire plant of the new variety.
Figure 2:
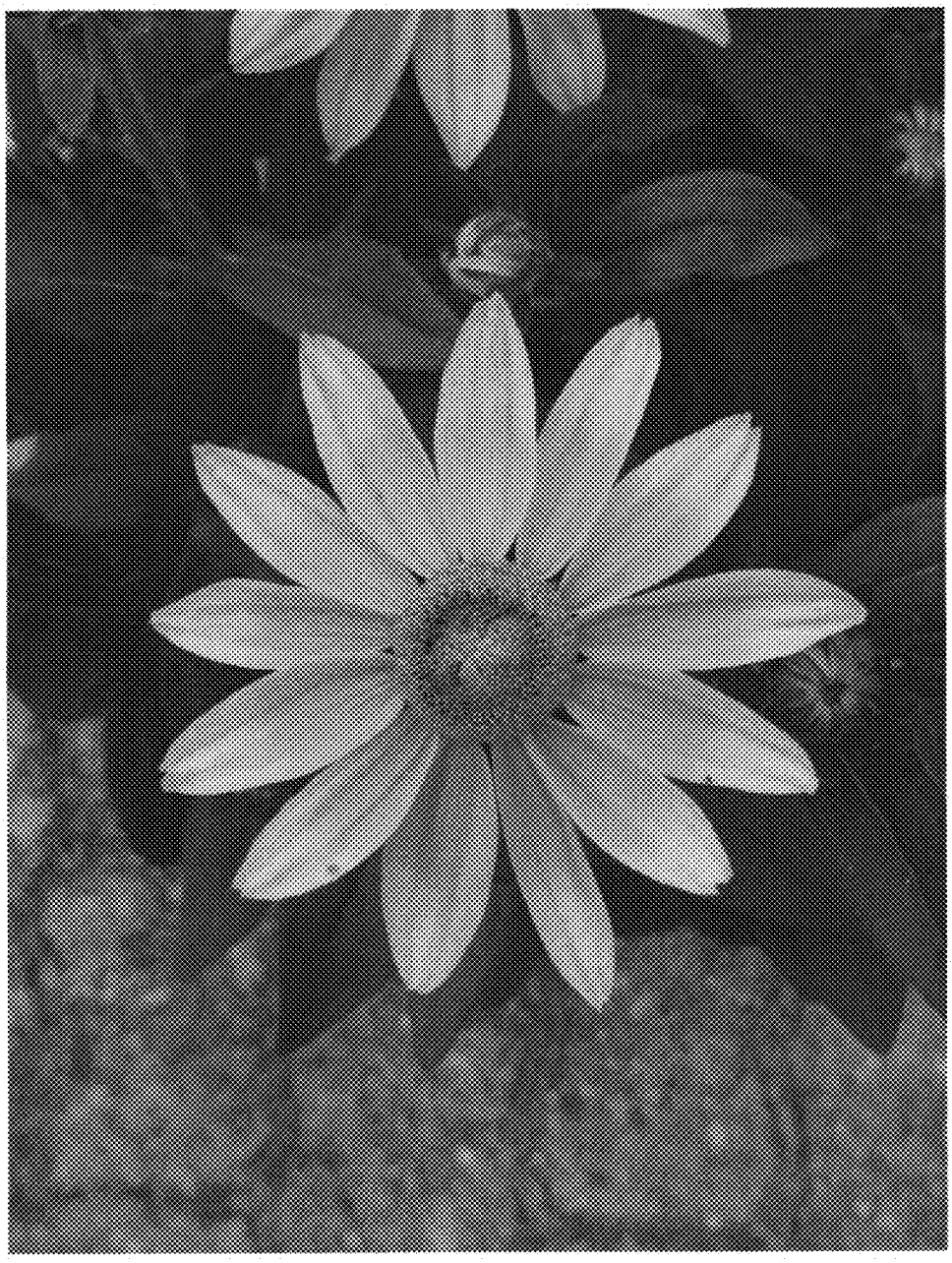
FIG. 2 shows a close-up view of a bloom of the new variety.

The following detailed description sets forth the characteristics of the new variety as the result of asexual reproductions performed via in vitro tissue culture in October of 2013 carried out in Gönnebeck, Germany. Plants of the new variety were grown outdoors in 21 cm (4 liter) pots, and the color readings and measurements were observed under natural light on 18 week old plants in Gönnebeck, Germany. Color references are primarily to The 2001 R.H.S. Colour Chart of The Royal Horticultural Society of London.

PLANT

Time to initiate roots: About 7-10 days at approximately 18° C.
Time to develop roots: About 38-45 days at approximately 16-18° C.
Time to produce a finished flowering plant from a rooted cutting: About 10-12 weeks in a 21 cm container.
Rooting habit: Exhibits numerous roots of medium thickness that are freely branching and close to White Group RHS 155B in color.
Plant height: About 50-65 cm.
Plant width: About 35-50 cm.
Vigor: Medium, with a compact growth habit.
Disease/pest resistance: Nothing unusual noted to date.
Temperature tolerance: From −5 to +40° C.
Drought tolerance: Average.
Branching habit: Exhibits one dominant strong branch with the biggest bloom and a few lateral side branches. All branches are semi-upright, forming a nice round habit.

Branches (flowering stems):
*Number per plant.*—10-25.
*Length.*—8-20 cm.
*Diameter.*—6-10 mm.
*Internode length.*—2-10 cm.
*Angle.*—Upright.
*Strength.*—Strong.
*Texture.*—Stable, with pubescence present.
*Color.*—Approximately Green Group RHS 137C.

Foliage:
*Arrangement.*—Alternate and simple.
*Leaf.*—Length: 9-22 cm. Width: 2-10 cm. Shape: Oblanceolate. Apex: Acuminate. Base: Attenuate to acute. Margin: Dentate and undulate. Texture: Upper surface: Rough, with pubescence present. Lower surface: Rough, with pubescence present. Color: Young leaves: Upper surface: Approximately Green Group RHS 137C. Lower surface: Approximately Green Group RHS 138B. Mature leaves: Upper surface: Approximately Green Group RHS 137C. Lower surface: Approximately Green Group RHS 138B. Petiole: None present. Veins: Venation type: Pinnate. Color: Upper surface: Approximately Yellow-Green Group RHS 145C. Lower surface: Approximately Yellow-Green Group RHS 145B.

INFLORESCENCE

Bud:
*Shape.*—Elliptic-shaped ray florets and tubular-shaped disc florets.
*Diameter.*—At least 3 cm.
*Length.*—At least 3 cm.
*Color.*—Approximately Yellow-Green Group RHS 151B.

Natural flowering season: Flowering occurs from the end of June to the middle of October in Germany, beginning approximately 8-10 weeks after planting.

Average number of inflorescences per plant: Numerous, 20-50.

Average number of inflorescences per branch: From 1-5.

Disc and ray floret arrangement: Disc florets are arranged in the middle of the receptacle of the inflorescence with ray florets extending outwardly therefrom.

Fragrance: Light to none present.

Inflorescence:
*Diameter.*—10-15 cm.
*Height (depth).*—2-3 cm.
*Diameter of disc.*—2.5-3.5 cm.
*Receptacle height.*—1-1.5 cm.
*Receptacle diameter.*—4-7 cm.

Ray florets:
*Number per inflorescence.*—12-15.
*Arrangement.*—In one or two whorls.
*Length.*—4-7 cm.
*Width.*—2-3 cm.
*Shape.*—Elliptical.
*Apex.*—Emarginate.
*Base.*—Acute.
*Margin.*—Entire.
*Texture.*—Upper surface: Smooth and glabrous. Lower surface: Rough.
*Color.*—When opening: Upper surface: Approximately Yellow-Orange Group RHS 21A, turning more yellow in color (approximately Yellow-Orange Group RHS 14A) toward the apex. Lower surface: Approximately Yellow-Orange Group RHS 15B, with a light shimmer of green (approximately Yellow-Green Group RHS 150A). At maturity: Upper surface: Approximately Yellow-Orange Group RHS 21A, turning more yellow in color (approximately Yellow-Orange Group RHS 14A) toward the apex. Lower surface: Approximately Yellow-Orange Group RHS 15B, with a light shimmer of green (approximately Yellow-Green Group RHS 150B). Ground color description: Approximately Yellow-Orange Group RHS 21A, turning more yellow in color (approximately Yellow-Orange Group RHS 14A) toward the apex.
*Venation.*—Appearance: Parallel. Color: Upper surface: Same color as the ray florets. Lower surface: Same color as the ray florets.

Disc florets:
*Number per inflorescence.*—Numerous; too many to quantify.
*Arrangement.*—In the center of receptacle.
*Length.*—About 5-10 mm.
*Width.*—About 1 mm.
*Shape.*—Tubular.
*Apex.*—Five-pointed.
*Color.*—Immature: Approximately Green Group RHS 138C. At maturity: Approximately Greyed-Orange Group RHS 163B.

Phyllaries:
*Number per inflorescence.*—20-35.
*Arrangement.*—In about three whorls.
*Length.*—1-3 cm.
*Width.*—3-8 mm.
*Shape.*—Lanceolate.
*Apex.*—Elongated oval.
*Base.*—Fused.
*Margin.*—Undulate.
*Texture.*—Upper surface: Rough, with pubescence present. Lower surface: Rough, with pubescence present.
*Color.*—Immature: Upper surface: Approximately Green Group RHS 138A. Lower surface: Approximately Green Group RHS 138B. At maturity: Upper surface: Approximately Green Group RHS 138A. Lower surface: Approximately Green Group RHS 138B.

Reproductive organs:

Androecium:
*Presence.*—On ray and disc florets.
*Number (per floret).*—Numerous.
*Filament length.*—1-2 mm.
*Filament color.*—Light green.
*Anther.*—Shape: Round. Length: 1 mm. Color: Light green.
*Pollen.*—Color: Approximately Yellow Group RHS 9A. Amount: Plentiful; too much to quantify.

Gynoecium:
*Presence.*—In ray and disc florets.
*Pistil length.*—About 2 mm.
*Stigma.*—Shape: Two-parted. Color: Yellow to light green.
*Style.*—Length: 1-2 mm. Color: Light green.

Seeds:

*Shape*.—Oval.

*Overall size*.—Approximately 2 mm.

*Color*.—Approximately Black Group RHS 202A.

I claim:

1. A new and distinct variety of *rudbeckia* plant named 'BullRudi 02', as is herein illustrated and described.

* * * * *